US009823207B2

(12) United States Patent
Wieskotten et al.

(10) Patent No.: US 9,823,207 B2
(45) Date of Patent: Nov. 21, 2017

(54) METHOD AND DEVICE FOR DETERMINING INTRACELLULAR AND/OR EXTRACELLULAR, IN PARTICULAR MACROMOLECULAR FRACTIONS OF FLUIDS, PREFERABLY OF BODY FLUIDS OF LIVING ORGANISMS

(75) Inventors: Sebastian Wieskotten, Ober-Ramstadt (DE); Tobias Groeber, Heusenstamm (DE); Paul Chamney, Herts (GB); Peter Wabel, Darmstadt (DE); Ulrich Moissl, Karben (DE)

(73) Assignee: FRESENIUS MEDICAL CARE DEUTSCHLAND GMBH, Bad Homburg (DE)

( * ) Notice: Subject to any disclaimer, the term of this patent is extended or adjusted under 35 U.S.C. 154(b) by 880 days.

(21) Appl. No.: 13/697,132

(22) PCT Filed: May 11, 2011

(86) PCT No.: PCT/EP2011/057604
§ 371 (c)(1),
(2), (4) Date: Jan. 31, 2013

(87) PCT Pub. No.: WO2011/144511
PCT Pub. Date: Nov. 24, 2011

(65) Prior Publication Data
US 2013/0134077 A1 May 30, 2013

(30) Foreign Application Priority Data

May 11, 2010 (DE) .................. 10 2010 028 902

(51) Int. Cl.
*B01D 35/00* (2006.01)
*G01N 27/00* (2006.01)
*A61M 1/36* (2006.01)
*G01N 33/487* (2006.01)

(52) U.S. Cl.
CPC ........... *G01N 27/00* (2013.01); *A61M 1/3626* (2013.01); *A61M 1/3669* (2013.01); *G01N 33/48735* (2013.01); *A61M 2205/3317* (2013.01)

(58) Field of Classification Search
None
See application file for complete search history.

(56) References Cited

U.S. PATENT DOCUMENTS 3,993,945 A * 11/1976 Warmoth ............... G01R 27/22
324/434
4,014,206 A 3/1977 Taylor
(Continued)

FOREIGN PATENT DOCUMENTS

DE 196 51 355 6/1998
DE 197 39 099 1/1999
(Continued)

OTHER PUBLICATIONS

Cole, KS; "Permeability and Impermeability of Cell Membranes for Ions"; 1940; Cold Spring Harbor Symp Quant Biol; 8; 110-122.*
(Continued)

*Primary Examiner* — Richard Gurtowski
(74) *Attorney, Agent, or Firm* — Jacobson Holman, PLLC.

(57) ABSTRACT

Method and device according to the method for determining intracellular and/or extracellular, in particular macromolecular fractions of fluids, preferably of body fluids of living organisms, with the steps:
coupling-in a measurement signal through an electrically non-conductive wall into the fluid to be measured;
coupling-out an electrical measurement value that is thereby generated in the fluid to be measured;
detecting the coupled-out electrical measurement value at a plurality of different frequencies of the electrical measurement signal;
determining the intracellular and/or extracellular, in particular macromolecular fractions of the fluid to be measured by means of evaluation of the detected electrical measurement value at a plurality of frequencies of the measurement signal.

23 Claims, 13 Drawing Sheets

(56) References Cited

U.S. PATENT DOCUMENTS

| | | | |
|---|---|---|---|
| 5,397,896 A * | 3/1995 | Weiss | B82Y 10/00 204/400 |
| 6,339,722 B1 | 1/2002 | Heethaar et al. | |
| 6,511,851 B1 | 1/2003 | Payne et al. | |
| 6,663,585 B1 | 12/2003 | Ender | |
| 2004/0065158 A1 | 4/2004 | Schrepfer et al. | |
| 2004/0197845 A1 * | 10/2004 | Hassibi | C12Q 1/04 435/8 |
| 2006/0033626 A1 * | 2/2006 | Collins | A61B 5/0537 340/573.1 |
| 2008/0065006 A1 | 3/2008 | Roger et al. | |

FOREIGN PATENT DOCUMENTS

| | | |
|---|---|---|
| DE | 696 23 304 | 7/2003 |
| EP | 1 645 227 | 4/2006 |
| WO | WO 93/18395 | 9/1993 |
| WO | WO 00/45697 | 8/2000 |
| WO | WO 02/25277 | 3/2002 |

OTHER PUBLICATIONS

Trebbels et al "Capacitive on-line hematocrit sensor design based on Impedance Spectroscopy for use in hemodialysis machines." 2009 Annual International Conference of The IEEE Engineering in Medicine and Biology Society, Sep. 3, 2009, pp. 1208-1211.

Vries et al. "Implications of the dielectrical behaviour of human blood for continuous online measurement of haematocrit." Medical and Biological Engineering and Computing, vol. 31, Nr. 5, Sep. 1, 1993, pp. 445-448.

Trebbels et al. "Hematocrit Measurement—A high precision on-line measurement system based on impedance spectroscopy for use in hemodialysis machines." IFMBE Proceedings 24/VII, pp. 247-250, 2009.

* cited by examiner

Fig. 12
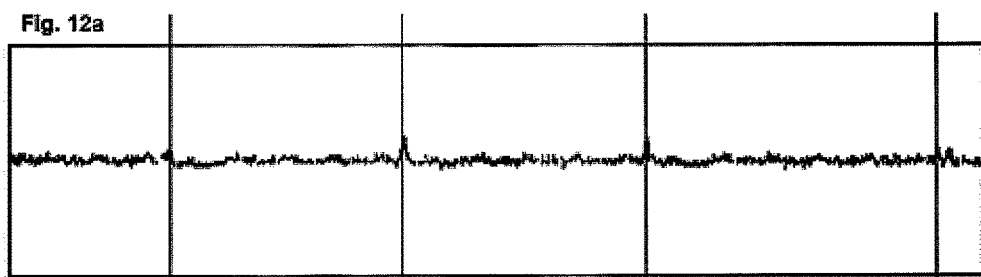
Fig. 12a
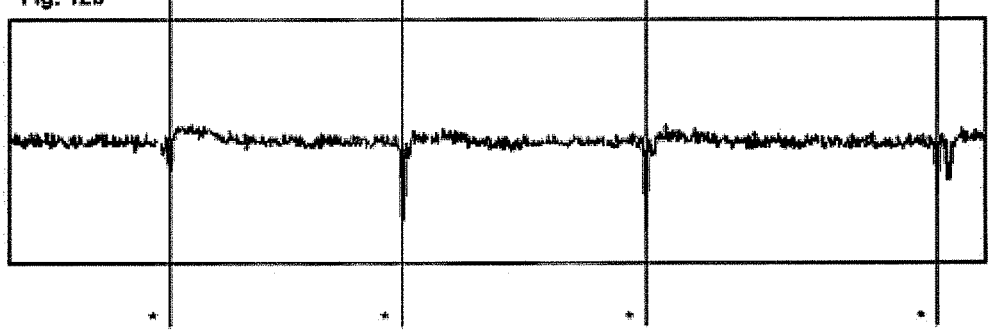
Fig. 12b

METHOD AND DEVICE FOR DETERMINING INTRACELLULAR AND/OR EXTRACELLULAR, IN PARTICULAR MACROMOLECULAR FRACTIONS OF FLUIDS, PREFERABLY OF BODY FLUIDS OF LIVING ORGANISMS This is a national stage of PCT/EP11/057604 filed May 11, 2011 and published in German, which has a priority of German no. 10 2010 028 902.7 filed May 11, 2010, hereby incorporated by reference.

FIELD OF THE INVENTION

The invention relates to a method and a device for determining parameters, in particular physiological and/or pathological parameters of fluids, preferably of body fluids, in particular in blood, of living organisms, which are suitable, among other uses, for the better control and regulation of dialysis machines. Specifically, a method and a device are proposed for determining intracellular and/or extracellular, in particular macromolecular fractions of fluids, preferably of body fluids, in particular of blood, of living organisms, by means of which the control and regulation of dialysis machines can be improved.

STATE OF THE ART

Dialysis is a method of purifying blood, which among other uses is employed as a replacement therapy in cases of kidney failure, in which mass transfer takes place through a semipermeable membrane, which is in contact on one side with the patient's blood and on the other with a dialysis solution (dialysate). This is intended to remove, among other substances, pyrogens, noxa, metabolites, and also excess water from the patient's blood by ultrafiltration. Water balancing during this transfer process, and monitoring of the hydration status of the patient during the dialysis procedure, are vital factors in the success of the dialysis and the welfare and health of the patient.

Therefore, in order to monitor the patient's hydration status during the dialysis, the state of the art uses for example a Body Composition Monitor manufactured by Fresenius Medical Care, in order to check the water content in the patient's body composition by means of bioimpedance measurement and use this to control and regulate the dialysis machine. For example, the patient's hydration status can be determined immediately prior to the dialysis treatment, and from this it is possible to deduce the volume of water which must be removed from the patient by ultrafiltration during a dialysis treatment. The ultrafiltration rate of the dialysis machine is to be set accordingly. A further example of the use of bioimpedance measurement to determine the hydration status of a dialysis patient and control a dialysis machine is described by EP 1 645 227 B1, which sets forth a method for controlling a dialysis machine wherein the hydration status of a patient is determined via bioimpedance measurement on a limb of the patient. However, a method of this type based on bioimpedance measurement works relatively indirectly (via tissue hydration/intracellular water), and thus does not enable rapid and precise feedback for the monitoring of a dialysis treatment.

In order to achieve a faster, more direct feedback, and control or regulation of the dialysis machine, the state of the art thus resorts to the hemoglobin concentration and/or the hematocrit value. For this purpose, in particular, the following methods are known:

a) the measurement of ultrasound transit times, e.g. the Blood Volume Monitor (BVM) from the company Fresenius Medical Care AG.
b) optical spectroscopy via the measurement of transmitted, absorbed, reflected and/or scattered light, e.g. the Blood Volume Sensor from the company Gambro GmbH, and the Hemoscan from the Hospal company.
c) with electrical contact: DeVries et al., in Med. & Biol. Eng. & Comp. 1993, 31, pp. 445-448, describe a method by which the impedance of blood flowing through a tube-shaped plastic segment with integrated measurement electrodes is measured, with the hematocrit value being determined from the measured value at a single measurement frequency.
d) without electrical contact: Trebbels et al., in IFMBE Proceedings 25/VII, pp. 247-250, 2009 describe a method for contactless determination of the hematocrit value by means of capacitive coupling. Here too, the hematocrit value is calculated via the measurement of capacitance from the reactance at a single frequency of 400 kHz, and offset with the measured value at 5 kHz for temperature compensation.

DISCLOSURE OF THE INVENTION

The object of the present invention is to provide a further continuously operating measurement method and a corresponding measurement device, for controlling or regulating a dialysis machine.

This object is achieved as regards the method by the method according to claim 1, and as regards the device by the device according to claim 9. In addition, a dialysis machine which uses the method according to the invention is described in claim 15. Some preferred embodiments are set forth in the respective dependent claims.

According to the present invention, in claim 1 a method for determining intracellular and/or extracellular fractions of fluids, preferably of body fluids of living organisms is set forth, with the steps:
 coupling-in a measurement signal through an electrically non-conductive wall into the fluid (3) to be measured;
 coupling-out an electrical measurement value that is thereby generated in the fluid (3) to be measured;
 detecting the coupled-out electrical measurement value at a plurality of frequencies of the electrical measurement signal;
 determining the intracellular and/or extracellular fractions of the fluid to be measured by means of evaluation of the detected electrical measurement value at a plurality of frequencies of the measurement signal.

The fluids are typically blood or other body fluids; it is also conceivable, however, to use the subject-matters of the invention for the analysis of dialysate (after the transfer process, downstream from the dialyzer), for the analysis of substitution body fluids, infusates, modified body fluids, and also for the analysis of solutions and preparations in the chemical and pharmaceutical industries. The subject-matter is explained hereinafter in terms of the analysis of blood. Vertebrate (and human) blood consists of intracellular and extracellular components. The intracellular components comprise the hematocrit (the proportion of all intracellular components in the blood volume), which is primarily determined by the concentration of hemoglobin-carrying erythrocytes. These intracellular components are suspended in the so-called blood plasma (referred to here as the extracellular component, comprising the entire "remainder" of the blood fluid without the intracellular components), which consists substantially of water, the electrolytes dissolved in the water (such as sodium, potassium, calcium, magnesium, chloride, phosphate and bicarbonate), glucose, and other inorganic and organic components. The (plasma) proteins (in particular albumins) may be allocated to the macromolecular component of the extracellular volume. The blood plasma can, however—for example as a consequence of incorrectly performed dialyses or infusions—also contain gas (air) bubbles.

The subject-matter of the invention aims to be able to detect and analyze physiological and/or pathological parameters in this complex "blend" of intracellular and extracellular components.

Further, in claim 9 a corresponding device for determining intracellular and/or extracellular, in particular macromolecular fractions of fluids, preferably of body fluids of living organisms, is provided, with:
- a coupling-in device (1, 2),
- a measurement signal generator (13), whose measurement signal can be coupled in via the coupling-in device (1, 2) through an electrically non-conductive wall into the fluid (3) to be measured;
- a coupling-out device (11, 12) by means of which an electrical measurement value that is generated by the coupled-in measurement signal in the fluid (3) to be measured can be coupled out through the electrically non-conductive wall (16);
- a detecting device (14) by means of which the coupled-out electrical measurement value can be detected,
- an evaluation device for determining the intracellular and/or extracellular, in particular macromolecular fractions of the fluid by means of calculation from a plurality of measurement values generated at different frequencies of the electrical measurement signal that are detected by the detecting device (14).

In the device set forth here it is possible to implement the coupling-in and coupling-out devices separately, or to provide combined coupling-in and coupling-out devices. In order to carry out the determination of intracellular and/or extracellular, in particular macromolecular fractions of fluids, it is necessary to supply measurement signals with at least two, preferably with at least three frequencies, particularly preferably with a continuous frequency spectrum. These frequencies can be applied either consecutively (sequentially) and separately measured, or else simultaneously as a complex periodic signal waveform or as a frequency mixture, whose Fourier spectrum contains multiple frequencies.

Finally, a dialysis machine with the device according to the invention is set forth in claim 15.

The advantages of the method and devices according to the invention are, among others, that a further continuously operating (or quasi-continuously operating) method is provided cost-effectively, by means of which a more precise balancing of the water transfer processes is made possible during the dialysis. The method proposed here also allows, for example, additional monitoring of the control or regulation of the dialysis machines, and two-way correction of measured values of hematocrit and protein. This makes it possible to increase the accuracy of the measured values and identify errors during the determination of measured values.

It is for example conceivable to apply the method proposed here in the extracorporeal circulation both upstream and downstream of the dialysis filter, and thereby use a direct comparison to balance the water transfer processes in the dialyzer, using these measured values for the control or regulation of the dialysis machine (for example via the adjustment of the transmembrane pressure in the dialysis chamber of the dialyzer). It is, however, also possible to carry out such regulation or control of the dialysis machine by determining the water content of the blood that has been treated by dialysis downstream of the dialyzer (before the venous blood return), and compare this with a desired value. It is furthermore possible to determine the protein concentration in the dialysate drain, in order to detect possible protein loss via the semipermeable dialysis membrane.

A further important advantage of the method proposed here is that it is possible to monitor the oncotic pressure, which is primarily determined by the colloid osmotic pressure of the proteins (particularly the albumin), and thereby be able to avoid hypotensive crises resulting from excessive ultrafiltration during the dialysis. In addition, the albumin concentration represents an important marker of the patient's nutritional status (low albumin concentration is an indicator of inadequate nutrition) and of the patient's inflammation status (low albumin concentration is a sign of inflammatory response).

Furthermore, the method and device according to the invention can also be used to detect—and for example initiate suitable action to counter—air bubbles and/or hemolysis in the treated blood, both of which can occur if dialysis is carried out incorrectly and which, if introduced into the blood circulation, can pose a serious risk to patients.

In a preferred embodiment of the method, the measurement signal can be an electrical, magnetic and/or electromagnetic alternating field, wherein the frequency of the alternating field is variable, preferably modulatable. This is an advantageous type of measurement signal, since an electrical, magnetic and/or electromagnetic field is capable of penetrating the electrically non-conductive wall surrounding the fluid to be measured, and generating measurement signals (electrical measured values) that are easy to detect and evaluate in the fluid to be measured. By using differing frequencies, preferably through frequency modulation of the alternating field, the complex fluid system can be analyzed according to several parameters, for example physiological and/or pathological parameters, wherein impedance spectroscopy (if necessary separated according to amplitude and phase) can also be carried out, by means of which particularly meaningful and precise results can be obtained. Alternatively, however, it is also conceivable to use a different type of sequential variation of the frequency of the alternating field (for example abrupt change), or to use a plurality of frequencies simultaneously (for example as a complex periodic signal waveform or as a frequency mixture, whose Fourier spectrum contains multiple frequencies).

In a further preferred embodiment of the method, at least the coupling-in of the measurement signal into the fluid (3) to be measured, preferably the coupling-in of the measurement signal into the fluid (3) to be measured and the coupling-out of the electrical measurement value thereby generated in the fluid to be measured, can take place capacitively and/or inductively. This is a particularly simple and expedient variant of the method, since by this means the coupling-in and coupling-out of the measurement signal and electrical measurement value can take place particularly precisely and without interference. In particular, lower frequencies of the measurement signal can be transmitted advantageously by means of inductive coupling. On the other hand, capacitive coupling, in contrast to inductive coupling, requires only that, for example, thin foil electrodes are stuck onto the outside of the wall of, for example, an extracorporeal blood tube in a dialysis machine, in order to achieve reliable coupling. In this case the electrodes can surround the blood tube in annular form over a length of a few millimeters or centimeters, in order to achieve as good a coupling as possible. It is, however, also conceivable to capture the electrical measurement value directly by means of contact electrodes.

In a further preferred embodiment of the method, at least a portion of the measurement signal can be capacitively coupled into the fluid to be measured, and at least a portion of the electrical measurement value that is thereby generated in the fluid (3) to be measured can be capacitively coupled out. Capacitive coupling represents a particularly simple and advantageous method of coupling-in and coupling-out the measurement signal and electrical measurement value respectively. This method can be employed exclusively or in combination with other coupling methods, particularly inductive coupling; in the latter case the different coupling methods can be used for measurement simultaneously or successively.

In a further preferred embodiment of the method, the coupling-in of the electrical measurement signal into the fluid to be measured can take place by means of a pair of coupling-in electrodes, and the coupling-out of the electrical measurement value thereby generated in the fluid to be measured can take place by means of a pair of coupling-out electrodes, preferably as four-point measurement. This arrangement enables a considerable improvement in the accuracy of measurement.

In a further preferred embodiment of the method, the coupling-in of the electrical measurement signal into the fluid (3) to be measured and the coupling-out of the electrical measurement value thereby generated in the fluid to be measured can take place capacitively and inductively. By this means the advantages of the two coupling methods can be combined, wherein inductive coupling can advantageously be employed for low frequencies, and capacitive coupling, due to the high-pass characteristics of the latter coupling method, for the higher frequencies. The different coupling methods can be used for measurement simultaneously or successively, wherein it is possible to combine the coupled-in measurement signal and/or the coupled-out electrical measurement value for both coupling methods, or to process them separately.

In a further preferred embodiment of the method, the determination of the intracellular and/or extracellular, in particular macromolecular fractions of fluids can comprise the detection of the electrical impedance of the fluid to be measured at a plurality of different frequencies of the electrical measurement signal according to amplitude and phase, preferably with high temporal resolution of the amplitude and phase. In this, a measuring current can for example be engendered in the fluid by means of a measurement signal which can be varied over time, and the voltage drop thus produced in the fluid can be measured. This represents a particularly advantageous measurement procedure, especially in terms of a high degree of accuracy of measurement and reduced susceptibility to interference. The accuracy of measurement can be still further increased by the separate evaluation of amplitude attenuation and phase shift. In order to achieve the greatest possible accuracy of measurement, it is expedient to detect the amplitude attenuation and phase shift of the electrical measurement signal with high temporal resolution. A suitable impedance analyzer can for example be used for this purpose.

In a further preferred embodiment of the method, the determination of intracellular and/or extracellular, in particular macromolecular fractions of fluids can comprise evaluation on the basis of the Cole model. The Cole model represents a simple description of the ohmic and capacitive ratios in two-compartment systems such as for example blood fluids, and thereby depicts the electrical ratios in an easily analyzable form with a good level of accuracy.

In a preferred embodiment of the device, the coupling-in device and/or the coupling-out device can have flat electrodes for capacitive coupling-in of the measurement signal and/or for capacitive coupling-out of the electrical measurement value that is generated in the fluid to be measured. This is a particularly simple and expedient variant of the method, since—in contrast to inductive coupling-in and coupling-out—it requires only for example thin foil electrodes to be stuck onto the outside of the wall of, for example, an extracorporeal blood tube in a dialysis machine, in order to achieve reliable coupling. In this case the electrodes can surround the blood tube in annular form over a length of a few millimeters or centimeters, in order to achieve as good a coupling as possible.

In a further preferred embodiment of the device, the coupling-in device can have a pair of coupling-in electrodes, and the coupling-out device can have a pair of coupling-out electrodes, wherein the coupling-out electrodes are substantially disposed between the coupling-in electrodes. This arrangement enables a considerable improvement in the accuracy of measurement.

In a further preferred embodiment of the device, the coupling-in and coupling-out electrodes can be disposed on the outside of a fluid line, preferably a fluid tube, in particular an extracorporeal blood tube, through which can be conveyed the fluid with the intracellular and/or extracellular, in particular macromolecular fractions that are to be determined. This is a particularly expedient arrangement for the use of the method in combination with dialysis machines.

In a further preferred embodiment of the device, the detecting device can have a device for detecting the impedance preferably according to amplitude and phase. In this case, a measuring current can for example be engendered in the fluid by means of a measurement signal which can be varied over time, and the voltage drop thus produced in the fluid can be measured. This represents a particularly advantageous measurement procedure, especially in terms of increased accuracy of measurement and reduced susceptibility to interference. The accuracy of measurement can be still further increased by the separate evaluation of amplitude attenuation and phase shift.

In a further preferred embodiment of the device, the coupled-out electrical measurement values can be evaluated in the evaluation device on the basis of the Cole model. The Cole model represents a simple description of the ohmic and capacitive ratios in two-compartment systems such as for example blood fluids, and thereby depicts the electrical ratios in an easily analyzable form with a good level of accuracy.

In addition, a dialysis device is set forth with at least one device for determining intracellular and/or extracellular, in particular macromolecular fractions of fluids, preferably of body fluids of living organisms, wherein the dialysis device can preferably be controlled or regulated depending on at least one determined intracellular and/or extracellular fraction of the fluid. Through the combination of the method according to the invention with dialysis machines, its merits can be advantageously exploited in this medical application. In this case the method can be employed either simply as an additional monitor, to collect more precise data, or also to control or regulate the dialysis machine. The method can for example be employed before and/or after the dialysis treatment in the extracorporeal blood circulation, or also in the dialysate drain to determine for example the transfer of protein.

In a further preferred embodiment of the dialysis device, the device can be disposed downstream of the dialyzer and be suitable for the determination of the water fraction, by means of which a transmembrane pressure in the dialysis device can be controlled or regulated. It is thereby possible to determine the desired water content in the blood directly, and for example adjust this via the control of the dialysis device. The relevant adjustment could take place for example via the control or regulation of the blood pump, dialysate pump or ultrafiltration pump of the dialysis device (via their influence on the transmembrane pressure in the dialysis cell) by means of direct feedback of the variable to be adjusted, namely the water content of the blood, by a control system.

The water content of the blood as determined using the device is thus compared with a desired value. If the water content of the blood is too high, the delivery rate of an ultrafiltration pump is for example increased, which in a known manner, on the dialysate side downstream of the dialysis filter, removes dialysis fluid from the dialysis fluid system and thereby raises the transmembrane pressure of the semipermeable membrane in the dialysis filter from the blood side to the dialysate side. As a result of this more water from the patient's blood is filtered via the semipermeable membrane in the dialysis filter onto the dialysis side, and thus the water content of the patient's blood downstream of the dialysis filter falls. Analogously, if the water content of the blood is too low the delivery rate of the ultrafiltration pump is decreased, as a result of which the water content of the patient's blood downstream of the dialysis filter increases. Constant comparison of the desired and actual values of the water content of the blood, and control of an ultrafiltration pump based on this, thus achieves the regulation of the water content of the blood to conform to a desired value (to be determined by a doctor).

In a further preferred embodiment of the dialysis device, the device can be disposed downstream of the dialyzer and be suitable for the detection of air bubbles and/or the detection of hemolysis; furthermore, should air bubbles and/or hemolysis be detected by the device, a warning signal can be triggered and/or the dialysis can be interrupted. When a dialysis is carried out, air bubbles can enter the venous drip chamber (bubble catcher) due to leaks in low pressure parts of the extracorporeal blood system (e.g. between the blood pump and the arterial patient connection, and in the region of the heparin injection pump), or due to sudden loss of pressure for example after the dialysis filter, or due to incomplete deaeration of the dialysis circulation. Such air bubbles pose a serious risk to the patient of embolisms. For this reason great importance attaches to the detection of air bubbles after the venous drip chamber and before the venous blood return. This embodiment makes it possible to monitor the extracorporeal blood circulation reliably for air bubbles, and immediately trigger a warning signal and/or stop the dialysis and/or interrupt the dialysis circulation, for example by means of automatic venous and arterial tube clamps. Particularly precise detection of air bubbles is possible in particular by means of the evaluation of a selectively captured phase shift of the electrical measurement value.

With this embodiment, the detection of hemolysis is also possible. (Hemolysis is the breaking apart or bursting of red blood cells (erythrocytes) in particular through mechanical stress (pressure loads, compression in a supply pump, for instance a peristaltic roller pump) and/or osmotic stress.) Excessive hemolysis can lead to a large increase in the potassium level in the blood serum (98% of the potassium present in the body is intracellular), which can cause dangerous cardiac arrhythmia. When red blood cells are destroyed, the intracellular components of the blood are reduced, with in particular the hematocrit (Hct), which is determined by the method, becoming lower. The proportion of intracellular hemoglobin, which can be determined by measurement at high frequency, also falls. This hemoglobin from the destroyed blood cells (erythrocytes) now dissolves in the plasma and raises the plasma's protein content, as can also be determined by the method. When quotients are formed and monitored, hemolysis becomes evident through an abrupt fall in the otherwise substantially constant quotients. The normal filtration of medium molecular proteins by the dialysis filter has little effect on the protein content of the plasma, because the large albumin and globulin molecules do not pass through the filter. When hemolysis is detected, it is for example possible immediately to trigger a warning signal and/or stop the dialysis and/or interrupt the dialysis circulation, for example by means of automatic venous and arterial tube clamps.

In a further preferred embodiment of the dialysis device, the intracellular and/or extracellular, in particular macromolecular fractions of fluids, can be determined before and after the dialysis treatment. Such differential measurement of the blood before and after the dialyzer can enable for example protein loss during the dialysis to be determined particularly exactly. More accurate balancing of the water removal in the dialyzer can also be carried out by this means. Finally, the information can also be used for regulating intradialytic nutrition: the nutrients (proteins and fats) in an intradialytic parenteral nutrition therapy (IDPN) are, due to their size, largely flushed out. Because of secondary layer formation in the course of a treatment, the patency of the dialyzer for the nutrients decreases, and for this reason IDPN is not advisable until near the end of the dialysis treatment. Using bolus administration of IDPN nutrients, impedance measurements before and after the dialyzer can determine what proportion of the nutrients are flushed out, and whether it is advisable to begin IDPN.

The invention is not limited by the particular embodiments; the features of all of the above-mentioned embodiments can be freely combined with each other, if and to the extent that they are not mutually exclusive for technical reasons and do not have negative effects on each other.

DESCRIPTION OF THE FIGURES

Two example embodiments of the invention are explained in detail below with the aid of the drawings. The drawings show:

FIG. 12b variation in the phase of the blood impedance at 1 Mhz (injection of air bubbles indicated by *)

Figure 1:
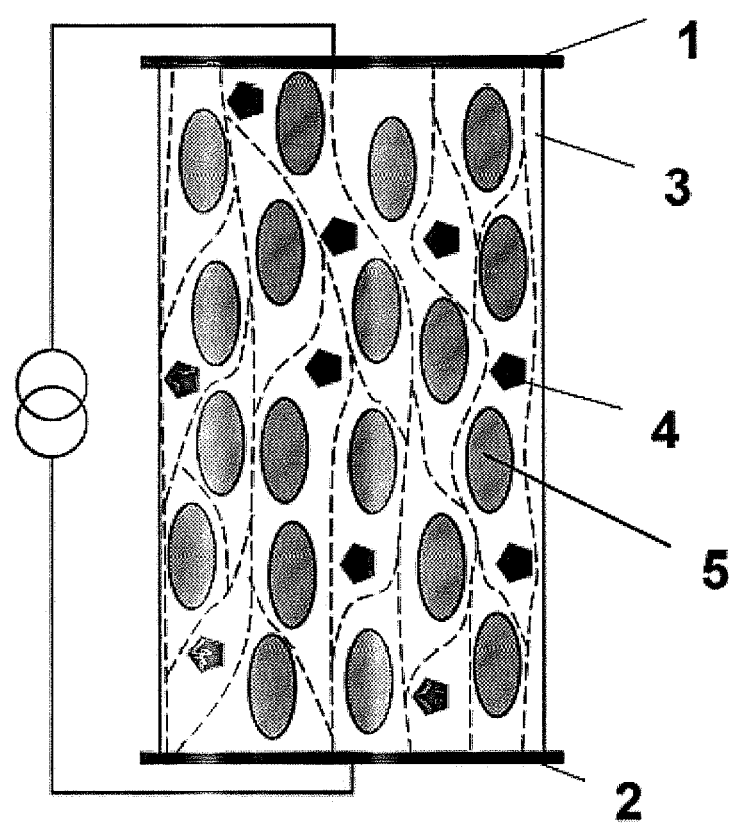
FIG. 1 current paths through a blood sample at a low measurement signal frequency FIG. 2 current paths through a blood sample at a high measurement signal frequency FIG. 3 Cole equivalent circuit diagram for the blood sample FIG. 4 idealized locus curve of blood in resistance-reactance diagram FIG. 5 equivalent circuit diagram for the measurement of impedance using a impedance analyzer FIG. 6 measured impedance locus curve ($Z_{disp}$) of 0.9% aqueous NaCl solution and of blood at variable ultrafiltration volumes FIG. 7 calculated impedance locus curve of blood at variable ultrafiltration volumes FIG. 8 comparison between the hemoglobin concentration and the calculated BIS factor (bioimpedance)
Figure 2:
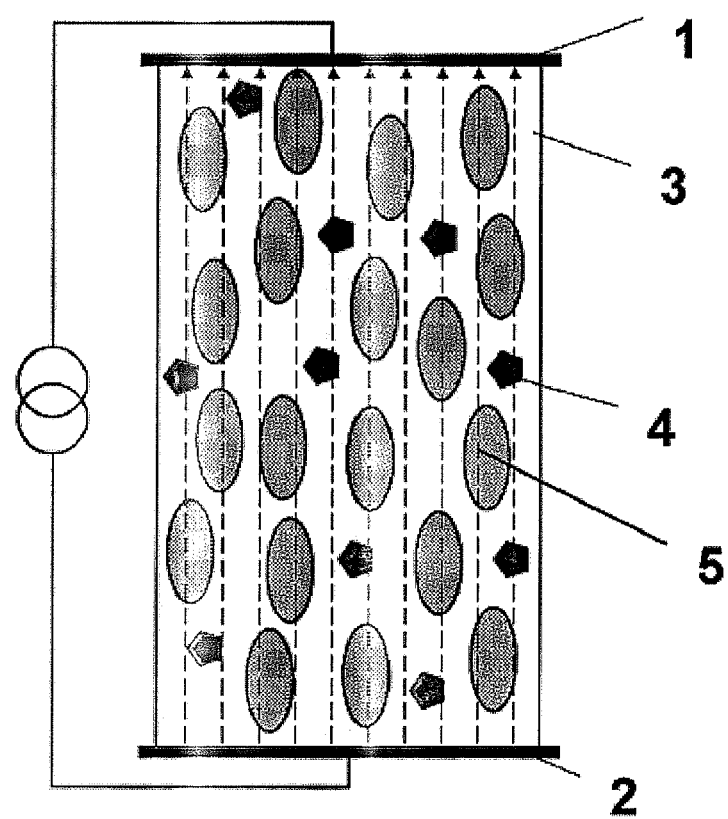
Figure 3:
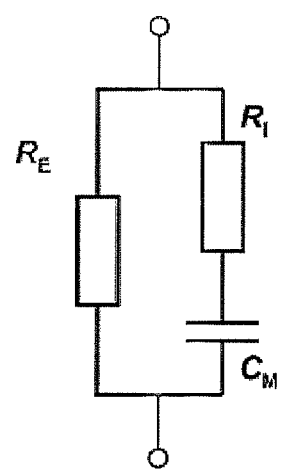
Figure 4:
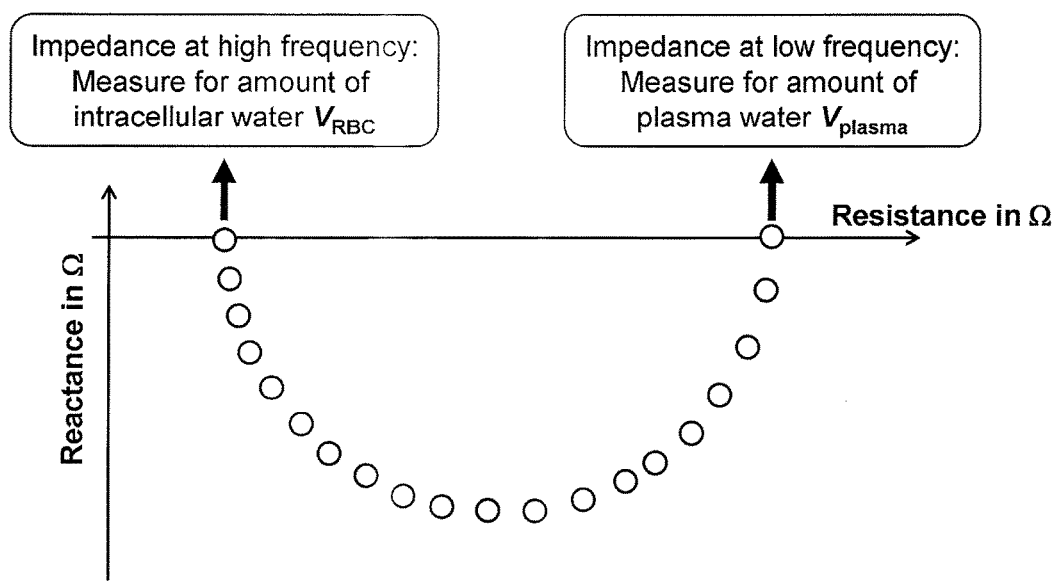

The measurement method proposed here is based in a first approximation on the assumption that blood is a suspension of blood cells 5 (predominantly red blood cells) in plasma water 3, containing primarily dissolved ions and protein molecules 4 (of which albumins are present in the greatest quantity). If one applies a measuring current with a low frequency between two electrodes 1, 2, the current flow occurs almost exclusively through the plasma water 3 (FIG. 1), while at a high frequency the measuring current flows through the plasma water 3 and the blood cells 5 (FIG. 2), because the cell membranes of the blood cells 5, which isolate direct current and have an effect similar to capacitors, represent negligible resistance for such high frequencies. Thus the known Cole model, consisting of an ohmic resistor connected in parallel with a series connection of an ohmic resistor and a capacitor (FIG. 3), can be used as an equivalent circuit diagram for such a blood sample. In a resistance-reactance diagram, there thus results, for a plurality of different measurement frequencies, an idealized locus curve as shown in FIG. 4, wherein the volume of plasma water $V_{plasma}$ can be calculated from the resistance $R_E$ and the volume of the erythrocytes $V_{RBC}$ from the volume $R_I$.

$$V_{plasma} = \left( \frac{l_{Schlauch} \cdot \sqrt{V_{total}}}{\rho_{plasma} \cdot R_E} \right)^{\frac{2}{3}}$$

$$= \left( \frac{l_{Schlauch} \cdot \sqrt{V_{total}}}{\rho_{plasma}} \right)^{\frac{2}{3}} \cdot \left( \frac{1}{R_E} \right)^{\frac{2}{3}}$$

$$= k_{plasma} \cdot (R_E)^{-2/3}$$

$$V_{RBC} = \left( \frac{l_{Schlauch} \cdot \sqrt{V_{total}}}{\rho_{RBC} \cdot R_I} \right)^{\frac{2}{3}}$$

$$= \left( \frac{l_{Schlauch} \cdot \sqrt{V_{total}}}{\rho_{RBC}} \right)^{\frac{2}{3}} \cdot \left( \frac{1}{R_I} \right)^{\frac{2}{3}}$$

$$= k_{RBC} \cdot (R_I)^{-2/3}$$

Formula 1, 2

Here the two values $I_{Schlauch}$ and $V_{total}$ are known from the measurement setup: $I_{Schlauch}$ is the length and $V_{total}$ the volume of the measurement area ["Schlauch"="tube" in German]. The conductivities of plasma water and erythrocytes are $\rho_{plasma}$ and $\rho_{RBC}$ respectively. Since length, volume and conductivity can if necessary be assumed to be constant, they can be combined into the constants $k_{plasma}$ and $K_{RBC}$, which can be determined experimentally. Using the known volumes $V_{total}$ and $V_{RBC}$, the hematocrit value Htc can be calculated from the determining equation:

$$Hct = (V_{RBC}/V_{total}) \times 100\%$$

Formula 3

If necessary, the hemoglobin concentration in the blood can be calculated from the Hct. With the known volumes $V_{total}$, $V_{RBC}$ and $V_{plasma}$, the volume of solids can be calculated. Assuming that the solids consist substantially of proteins, the volume of proteins in the blood $V_{protein}$ is consequently determined:

$$V_{protein} = V_{total} - V_{RBC} - V_{plasma}$$

Formula 4

If one assumes that the solids consist substantially of proteins, the density of protein ($D_{protein}=1.4$ kg/l) can be used to calculate the plasma protein concentration $C_{protein}$:

$$c_{protein} = (V_{protein} \times D_{protein})/V_{plasma}$$

Formula 5

Thus it is possible from a bioimpedance measurement of the blood to determine the protein concentration, the hematocrit value, and if necessary the hemoglobin concentration.

Figure 5:
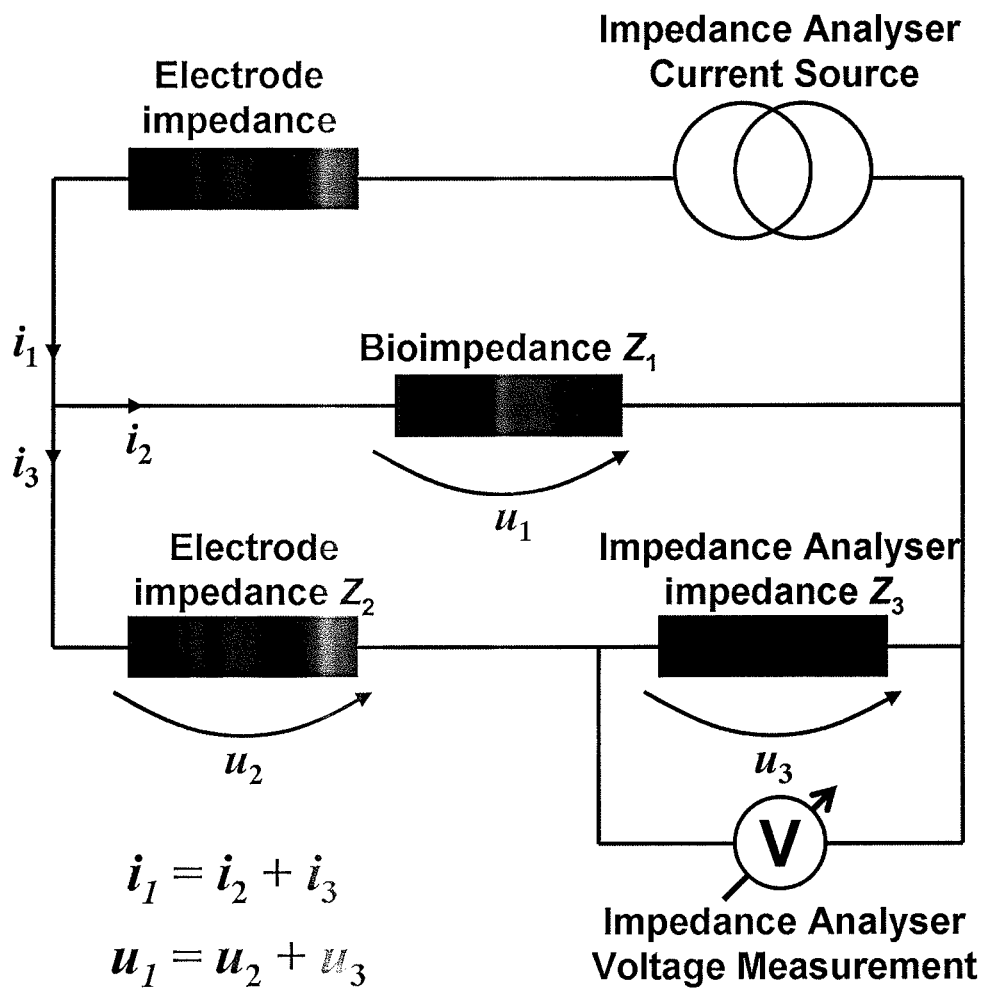

FIG. 5 shows the circuit diagram of an impedance analyzer for the determination of a bioimpedance $Z_1$: via the electrodes with the impedance $Z_2$, the current source and voltage electrodes of the impedance analyzer are connected to the bioimpedance. The impedance analyzer itself has the internal resistance (or internal impedance) $Z_3$, over which the voltage drop is measured.

Assuming that the internal resistance of the impedance analyzer is significantly greater than the bioimpedance $Z_1$ to be measured, the major part of the measuring current $i_1$ flows over the bioimpedance, and the voltage drop $u_3$ measured by the BCM corresponds to the voltage drop over the bioimpedance $u_1$. The voltage $Z_{disp}$ indicated by the BCM is calculated according to:

$$Z_{disp} = u_3/i_1$$

Formula 6

If the bioimpedance is sufficiently low compared to the internal resistance, $Z_{disp}$ corresponds to the bioimpedance $Z_1$. If this is not the case, because the bioimpedance assumes values that are too high, the measured impedance $Z_{disp}$ no longer corresponds to the bioimpedance $Z_1$.

Figure 6:
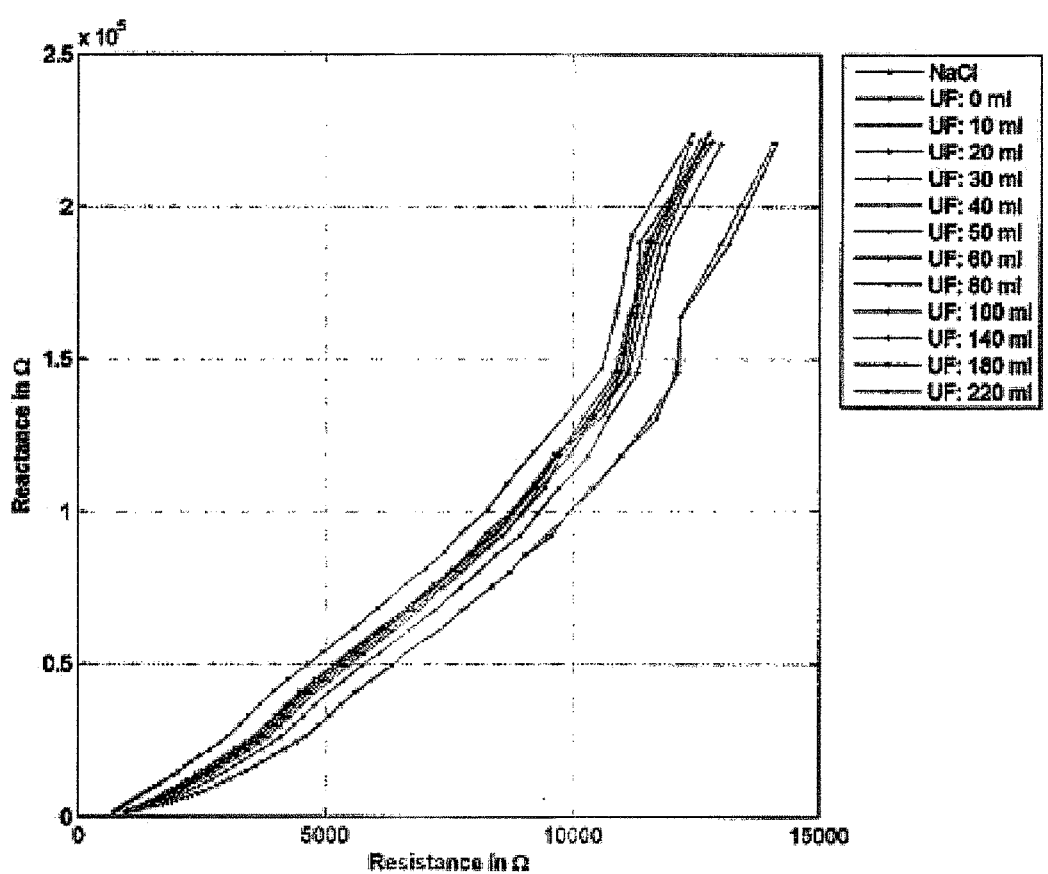

This is the case when the impedance of blood in the blood tube is measured with capacitive coupling. FIG. 6 shows such impedance locus curves when measuring either a 0.9% NaCl solution or blood concentrated by ultrafiltration in the blood tube:

With the aid of a voltage divider and a current divider, the resistance ratio, which corresponds to the indicated impedance $Z_{disp}$, can be calculated:

$$\frac{u_3}{u_1} = \frac{Z_3}{Z_2 + Z_3} \Rightarrow u_3$$

$$= u_1 \cdot \frac{Z_3}{Z_2 + Z_3}$$

$$\frac{i_2}{i_1} = \frac{Z_2 + Z_3}{Z_1 + Z_2 + Z_3} \Rightarrow i_1$$

$$= i_2 \cdot \frac{Z_1 + Z_2 + Z_3}{Z_2 + Z_3}$$

$$= \frac{u_2}{Z_1} \cdot \frac{Z_1 + Z_2 + Z_3}{Z_2 + Z_3}$$

$$Z_{disp} = \frac{u_3}{i_1}$$

$$= \frac{Z_1 \cdot Z_3}{Z_1 + Z_2 + Z_3}$$

Formula 7-9

When the bioimpedance $Z_1$ is known, for example in the case of 0.9% aqueous NaCl solution in the tube, the internal resistance of the BCM $Z_3$ can be calculated from the indicated impedance $Z_{disp}$ with the aid of Formula 4.

Figure 7:
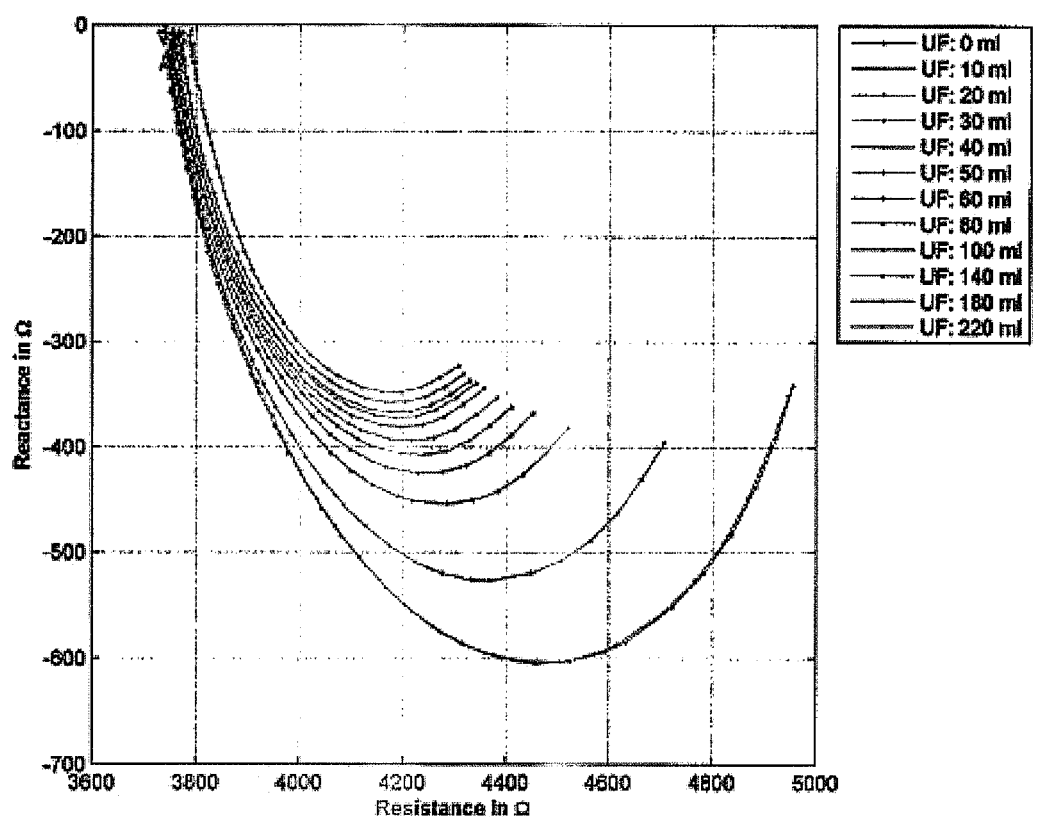

When the impedances $Z_3$ (determined with the aid of a 0.9% aqueous NaCl solution) and $Z_2$ (from the electrode geometry) are known, the bioimpedance $Z_1$ can be calculated by means of Formula 4. FIG. 7 shows this for the concentrated blood:

In the next step, the volumes of erythrocytes $V_{RBC}$ and plasma water $V_{plasma}$ can be calculated from the resistances.

$$V_{plasma} = k_{RBC} \cdot (R_I)^{-2/3}$$

$$V_{plasma} = k_{plasma} \cdot (R_E)^{-2/3} \quad \text{Formula 10, 11}$$

When the total volume $V_{total}$ is known, it can be used with $V_{RBC}$ to calculate the hematocrit value Htc:

$$Hkt = \frac{V_{RBC}}{V_{total}} = k_{Hkt} \cdot (R_I)^{-2/3} \quad \text{Formula 12}$$

Figure 8:
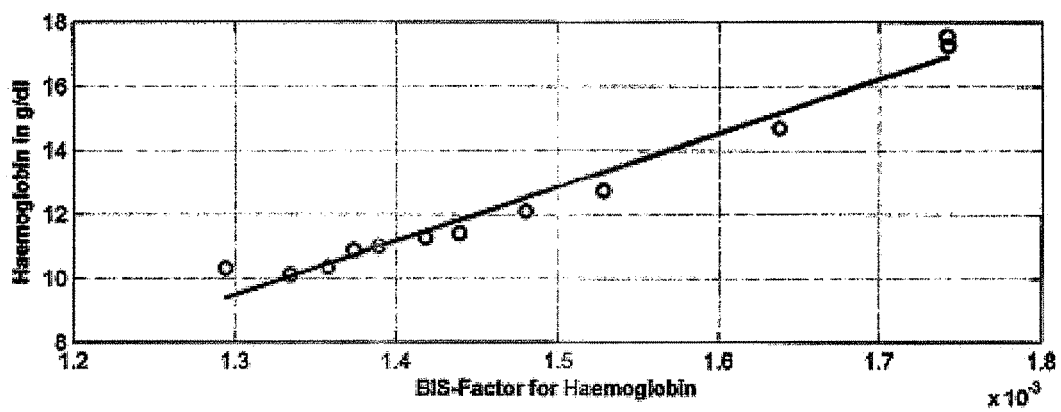

That is to say, Hct is related to the Cole resistance $R_I$. In the laboratory experiment, the hemoglobin concentration in the blood, rather than the hematocrit value, was determined; the two values are, however, closely correlated. FIG. 8 shows the relationship between the hemoglobin concentration and the BIS factor (without $k_{Hct}$) given in Formula 12:

The theoretically expected linear relationship between the BIS factor and the hemoglobin concentration can be clearly discerned.

For the concentration of plasma proteins the following applies:

$$c_{protein} = D_{protein} \cdot \frac{V_{protein}}{V_{plasma}} = D_{protein} \cdot \quad \text{Formula 13}$$

$$\frac{V_{total} - V_{RBC} - V_{plasma}}{V_{total} - V_{RBC}} \propto k_{pro} \cdot \frac{1 - (R_E)^{-2/3} - (R_I)^{-2/3}}{1 - (R_I)^{-2/3}}$$

Figure 9:
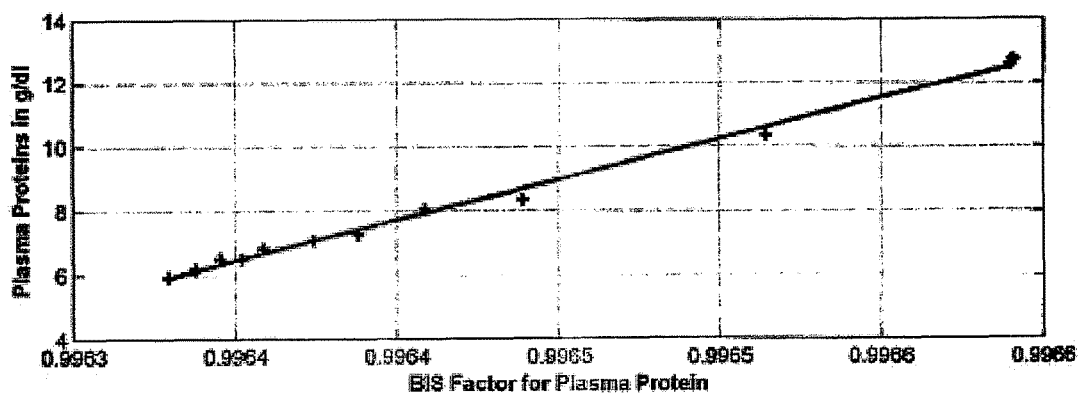
FIG. 9 comparison between the plasma protein concentration and the calculated BIS factor (bioimpedance)

If one plots this factor against the plasma protein concentrations measured in the laboratory (FIG. 9), one again obtains a linear relationship, as theoretically expected.

These two linear relationships can be used to determine, with the aid of the bioimpedance, the concentrations of plasma proteins and hemoglobin, and/or the hematocrit value, in "real time" during the dialysis.

Figure 10A:
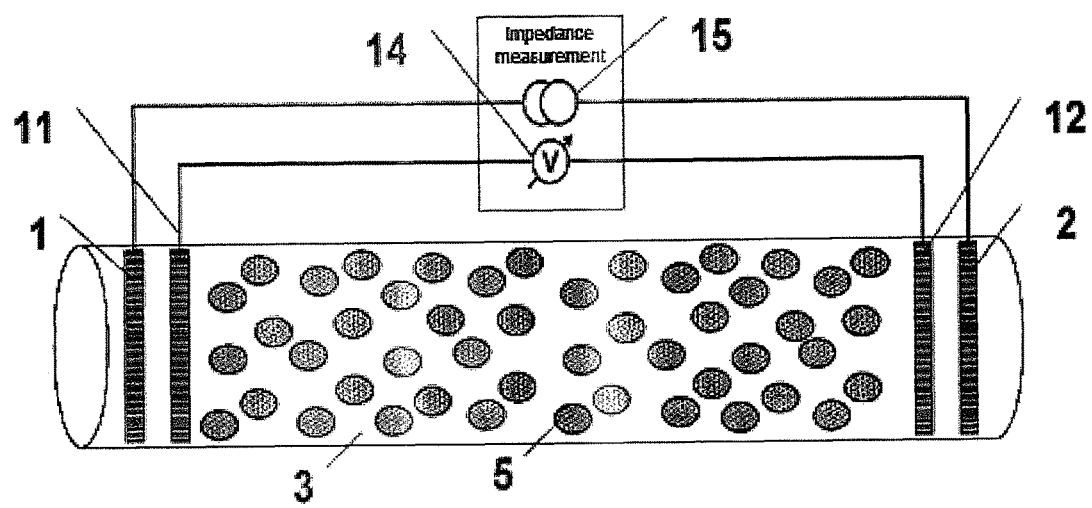
FIG. 10a schematic diagram of the measurement setup for determining the blood impedance FIG. 10b practical measurement setup for determining the blood impedance (blood tube with BCM electrodes applied)
Figure 10B:
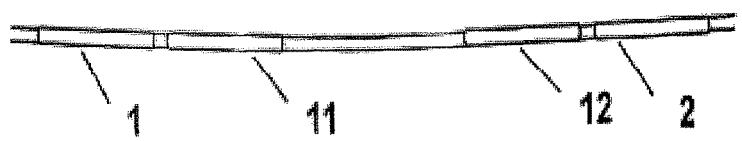
Figure 11:
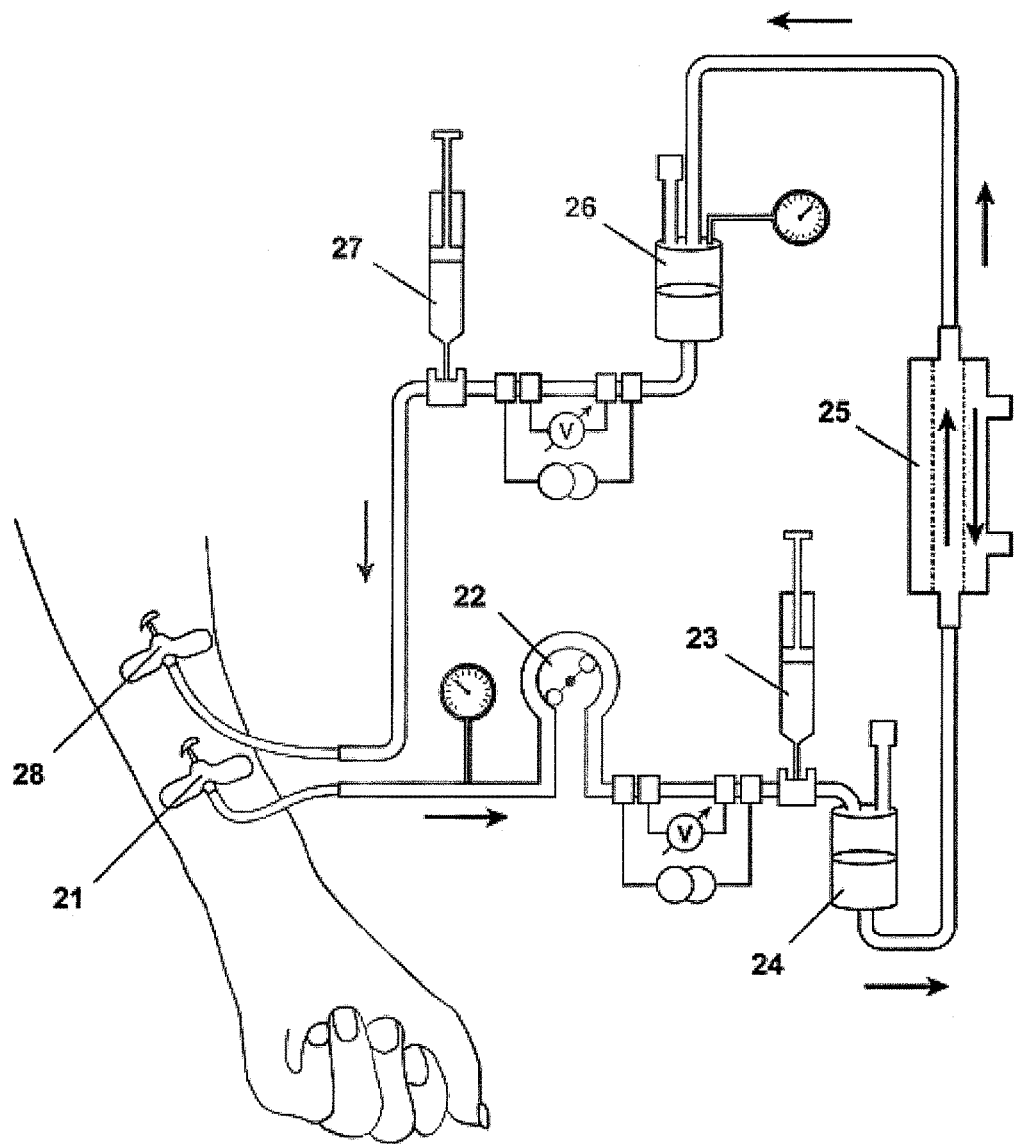
FIG. 11 schematic diagram of a dialysis machine with devices for determining the blood impedance before and after the dialyzer FIG. 12a variation in the amplitude of the blood impedance at 1 Mhz (injection of air bubbles indicated by *)

By way of an example, a particular embodiment in connection with a dialysis machine is described below with the aid of FIGS. 10a and 10b along with FIG. 11:

FIG. 11 is a schematic diagram of the blood flow in a typical dialysis arrangement with an arterial blood withdrawal 21, blood pump (peristaltic roller pump) 22, heparin feed 23, arterial bubble catcher 24, dialyzer 25, venous bubble catcher 26, injection port 27 and venous blood return 28. Devices are incorporated before and after the dialyzer for determining intracellular and/or extracellular fractions of fluids in the extracorporeal blood circulation. These comprise: coupling-in electrodes 1, 2, for coupling in the measurement signal (measuring current) from the measurement signal generator 13 into the blood to be measured, and coupling-out electrodes 11, 12, for coupling out the voltage drop (measurement signal) produced in the blood by the measuring current, with the voltage drop being measured by a detecting device 14. Not shown is the evaluation device, by means of which the intracellular and/or extracellular, in particular macromolecular fractions of fluids are calculated from the voltage drops and/or phase shifts at different measurement frequencies.

In order to determine intracellular and/or extracellular fractions of fluids in plasma water during the dialysis, and use these fractions expediently for monitoring, controlling and/or regulating the dialysis, the bioimpedance of the blood must be measured continuously or periodically at short time intervals. The coupled-in measurement signal is an electrical, electromagnetic and/or magnetic alternating field, which is frequency-modulated (wobbled) over a wide bandwidth (10 Hz to 10 MHz, preferably 1 kHz to 1 MHz, particularly preferably 5 kHz to 1 MHz). The detection of the electrical measurement value is carried out by means of a device for processing measurement values with high amplitude resolution and temporal resolution, using correlation with the coupled-in measurement signal, for example by means of a impedance analyzer, in order to be able to carry out the determination of the impedance according to amplitude and phase with a high resolution.

The measurement should preferably be carried out without galvanic contact between electrode and blood. Thus a pair of electrodes 1, 2 for capacitive injection of a measuring current, and a pair of electrodes 11, 12 for capacitive measurement of the voltage drop, are applied to the blood tube.

With the arrangement shown here it is additionally possible to detect air bubbles and blood clots in the blood tube. For this purpose, measurement for example at a frequency of 1 MHz and with a sampling rate of 30 samples per second can be carried out continuously. In this a small electrode spacing, of for example 20 mm, is advantageous.

The amplitude $|Z_{blood}|$ and the phase angle $\phi_{blood}$ of the blood impedance are obtained in this manner:

$$Z_{blood} = |Z_{blood}| * e^{i\phi_{blood}}$$

Then the moving average for the amplitude of $\overline{|Z_{blood}|}$ and the phase angle $\overline{\phi_{blood}}$ over the last 64 values is calculated:

$$\overline{|Z_{blood}|}(t) = \frac{1}{64} \sum_{k=1}^{64} |Z_{blood}|(t-k) \quad \text{Formula 15, 16}$$

$$\overline{\varphi_{blood}}(t) = \frac{1}{64} \sum_{k=1}^{64} \varphi_{blood}(t-k)$$

The differences between the moving average and the present measured value $\Delta|Z_{blood}|$ and $\Delta\overline{\phi_{blood}}$ show abrupt changes in blood impedance on the passage of air bubbles or clots.

$$\Delta|Z_{blood}| = |Z_{blood}| - \overline{|Z_{blood}|}$$

$$\Delta\overline{\phi_{blood}} = \phi_{blood} - \overline{\phi_{blood}}$$

FIG. 12a (top) shows the difference in the amplitude, and FIG. 12b (bottom) the difference of the phase angle, in the measured blood impedance when air bubbles are injected (at the points indicated by asterisks (*)) into the blood tube through a septum. In the measurement shown here 0.9% saline solution was used instead of blood; the delivery rate of the blood pump was 600 ml/min.

The injection of the air bubbles into the blood tube thereby becomes particularly apparent through a change in the phase angle.

The arrangement shown here also enables the reliable detection of any hemolysis which might occur in the blood in the blood tube. In this case, when red blood cells are destroyed there is a reduction in the intracellular components of the blood, in particular in the hematocrit (Hct), which can be determined reliably by the method.

At the same time there is a decrease in the intracellular hemoglobin fraction, which can preferably be determined by measurement at high frequency. This hemoglobin from the destroyed blood cells dissolves in the plasma and raises the plasma's protein content, which can likewise be determined by the method. When quotients are formed and monitored, hemolysis becomes evident through a sudden fall in the otherwise substantially constant quotients. The standard filtration of medium molecular proteins by the dialysis filter has little influence on the protein content of the plasma, since the large albumin and globulin molecules do not pass through the filter. Thus the quotient from the hemoglobin mass and the plasma protein mass remains constant in normal cases, i.e. when the dialysis treatment of the blood is correct (without damage to the erythrocytes):

$$\text{const.} = m_{Hb}/m_{pro} = (V_{blood} * c_{Hb})/(V_{plasma} * c_{Pro}) = c_{Hb}/((1-Hct) * c_{Pro})$$

Figure 13:
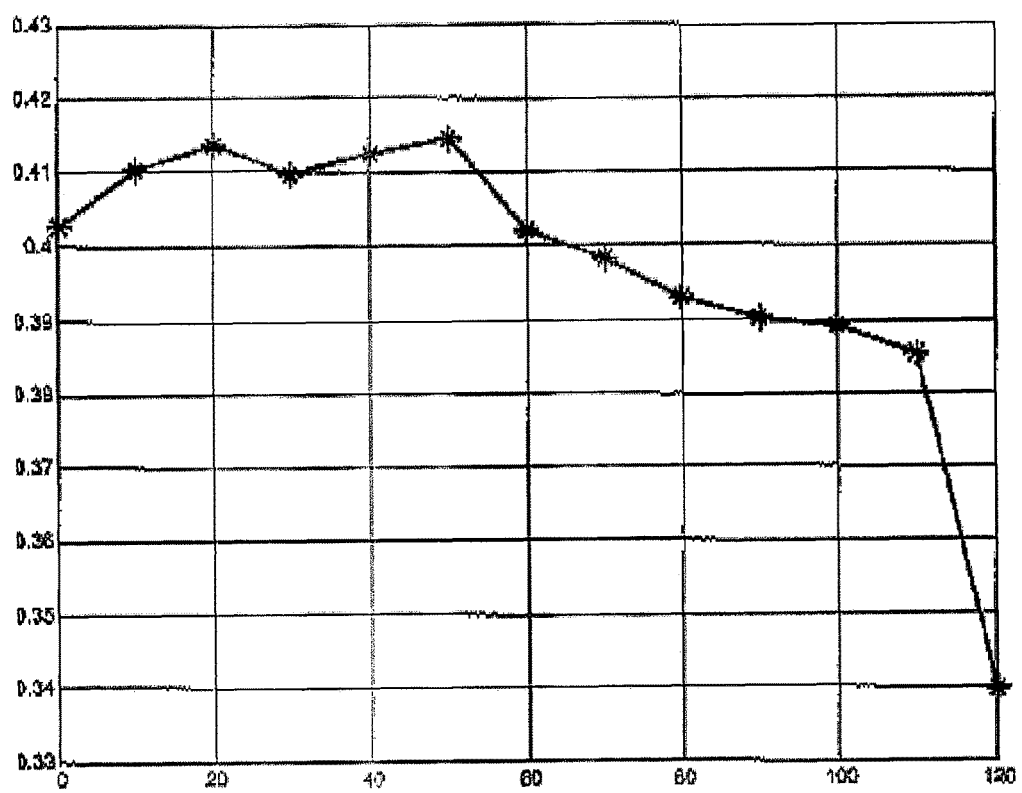
FIG. 13 variation in the $m_{Hb}/m_{pro}$ quotient on occurrence of hemolysis (abscissa values above 110)

When hemolysis occurs, however, there is a fall in $m_{Hb}$ and a simultaneous rise in $m_{pro}$, resulting in a dramatic change in their quotient, as shown in FIG. 13 (abscissa values above 110).

As well as measurement by means of capacitive coupling-in of the measurement current as described above, analogous contact-free measurement using inductive coupling-in of the measurement current via an exterior coil (coupling coil) is also conceivable for the person skilled in the art. Using the coil, magnetic fields of different frequencies are thereby generated outside the blood tube. As a measurement signal, the magnetic field that arises can for example be measured from outside using a GMR sensor (giant magnetoresistance sensor).

Due to the magnetic field injected, eddy currents are generated in the measurement area, which counteract the injected magnetic field. At low frequencies of the magnetic field, only small eddy currents form in both the extracellular and intracellular space, because the currents cannot pass through the cell membranes. The attenuation of the injected magnetic field is therefore only slight, and the GMR sensor would measure only a slight diminution of the magnetic field. At higher frequencies of the magnetic field, the eddy currents can pass through the cell membranes, and the injected magnetic field is attenuated to a greater extent. The measurement of the magnetic field influenced by the induced eddy currents is also possible in a known manner using other magnetic field sensors (e.g. Hall sensors or receiver coils).

Capacitive measurement forms a high-pass filter, and is therefore particularly suitable for higher frequencies. Thus in an alternative embodiment the low-frequency end of the measurement signal spectrum is coupled-in inductively by means of coupling coils (not shown), and the electrical measurement value thereby generated in the fluid to be measured is likewise coupled-out inductively by means of coupling coils (not shown). In contrast, the high-frequency end of the measurement signal spectrum is coupled-in capacitively, as shown in FIG. 11, by means of flat electrodes 1, 2, and the electrical measurement value thereby generated in the fluid to be measured is likewise coupled-out capacitively by means of flat electrodes 11, 12, so that in this case capacitive and inductive coupling on the excitation and measurement sides are used alongside each other, simultaneously or intermittently.

LIST OF REFERENCE SIGNS 1. coupling-in electrode
2. coupling-in electrode
3. fluid, blood
4. protein
5. blood cells
11. coupling-out electrode
12. coupling-out electrode
13. measurement signal generator
14. detecting device
15. blood tube
16. wall of the blood tube
21. arterial blood withdrawal
22. blood pump
23. heparin feed
24. arterial bubble catcher
25. dialyzer
26. venous bubble catcher
27. injection port
28. venous blood return

The invention claimed is:
1. Method for determining intracellular and extracellular fractions of a fluid using a device, wherein the device comprises
 a coupling-in device,
 a measurement signal generator, whose measurement signal can be capacitively and inductively coupled in, simultaneously or alternatively, via the coupling-in device through an electrically non-conductive wall into the fluid to be measured,
 a coupling-out device by which an electrical measurement value that is generated by the coupled-in measurement signal in the fluid to be measured can be capacitively and inductively coupled out, simultaneously or alternatively, through the electrically non-conductive wall,
 a detecting device configured for detecting the coupled-out electrical measurement value, and
 an evaluation device configured for determining the intracellular and extracellular fractions of the fluid by calculation from a plurality of measurement values generated at different frequencies of the measurement signal that are detected by the detecting device,
 wherein the inductive coupling-in is employed for frequencies of the measurement signal lower than the frequencies of the measurement signal for which the capacitive coupling-in is employed, and
 wherein the inductive coupling-in is supplied by at least one coupling coil,
the method comprising the steps of:
 coupling-in with the coupling-in device a measurement signal generated by the measurement signal generator through the electrically non-conductive wall into the fluid to be measured;
 coupling-out with the coupling-out device an electrical measurement value that is thereby generated in the fluid to be measured;
 detecting with the detecting device the coupled-out electrical measurement value at a plurality of frequencies of the measurement signal; and
 determining with the evaluation device at least one of the intracellular and extracellular fractions of the fluid to be measured by evaluation of the detected electrical measurement value at a plurality of frequencies of the measurement signal.

2. Method according to claim 1, characterized in that the measurement signal is at least one of an electrical, magnetic, and electromagnetic alternating field, wherein the frequency of the alternating field is variable and modulatable.

3. Method according to claim 1, characterized in that each of the coupling-in of the measurement signal into the fluid to be measured, and the coupling-out of the electrical measurement value thereby generated in the fluid to be measured, takes place capacitively, inductively, or capacitively and inductively.

4. Method according to claim 1, characterized in that at least a portion of the measurement signal is capacitively coupled into the fluid to be measured, and at least a portion of the electrical measurement value thereby generated in the fluid to be measured is capacitively coupled out.

5. Method according to claim 1, characterized in that the coupling-in device has at least one pair of coupling-in electrodes, and the coupling-out device has at least one pair of coupling-out electrodes, and characterized in that the capacitive coupling-in of the measurement signal into the fluid to be measured takes place by using the pair of coupling-in electrodes, and the coupling-out of the electrical measurement value thereby generated in the fluid to be measured takes place by using the pair of coupling-out electrodes as four-point measurement.

6. Method according to claim 1, characterized in that each of the coupling-in of the measurement signal into the fluid to be measured, and the coupling-out of the electrical measurement value thereby generated in the fluid to be measured, takes place capacitively, inductively, or capacitively and inductively.

7. Method according to claim 1, characterized in that the determining at least one of the intracellular and extracellular fractions of the fluid comprises detecting electrical impedance of the fluid to be measured at a plurality of different frequencies of the measurement signal according to amplitude and phase.

8. Method according to claim 1, characterized in that the determining at least one of the intracellular and extracellular fractions of the fluid comprises evaluation on the basis of the Cole model.

9. Device configured for determining intracellular and extracellular fractions of a fluid comprising
a coupling-in device,
a measurement signal generator, whose measurement signal can be capacitively and inductively coupled in, simultaneously or alternatively, via the coupling-in device through an electrically non-conductive wall into the fluid to be measured,
a coupling-out device by which an electrical measurement value that is generated by the coupled-in measurement signal in the fluid to be measured can be capacitively and inductively coupled out, simultaneously or alternatively, through the electrically non-conductive wall,
a detecting device configured for detecting the coupled-out electrical measurement value,
an evaluation device configured for determining the intracellular and extracellular fractions of the fluid by calculation from a plurality of measurement values generated at different frequencies of the measurement signal that are detected by the detecting device,
wherein the inductive coupling-in is employed for frequencies of the measurement signal lower than the frequencies of the measurement signal for which the capacitive coupling-in is employed, and
wherein the inductive coupling-in is supplied by at least one coupling coil.

10. Device according to claim 9, characterized in that the coupling-in device and/or the coupling-out device have flat electrodes for capacitive coupling-in of the measurement signal and for capacitive coupling-out of the electrical measurement value that is generated in the fluid to be measured and/or at least one coil for the inductive coupling-in of the measurement signal and/or at least one sensor for the measurement of a magnetic field influenced by an electrical value generated in the fluid to be measured.

11. Device according to claim 9, characterized in that the coupling-in device has at least one pair of coupling-in electrodes, and the coupling-out device has at least one pair of coupling-out electrodes, wherein the coupling-out electrodes are substantially disposed between the coupling-in electrodes.

12. Device according to claim 11, characterized in that the coupling-in and coupling-out electrodes are disposed on the outside of a fluid line which conveys the fluid with the intracellular and extracellular fractions that are to be determined.

13. Device according to claim 9, characterized in that the detecting device has a device for detecting an impedance according to amplitude and phase.

14. Device according to claim 9, characterized in that the coupled-out electrical measurement values can be evaluated in the evaluation device on the basis of the Cole model.

15. Dialysis machine comprising a dialyser and at least one device according to claim 9, wherein the dialysis machine is configured to be controlled or regulated depending on the determined intracellular and extracellular fractions of the fluid.

16. Dialysis machine according to claim 15, characterized in that the device is disposed downstream of the dialyzer and is configured for determination of a water fraction, which controls or regulates a transmembrane pressure in the dialysis device.

17. Dialysis machine according to claim 15, characterized in that the device is configured for detection of air bubbles and/or detection of hemolysis, and if air bubbles and/or hemolysis are detected during a dialysis circulation, a warning signal is triggered and/or the dialysis circulation is interrupted by the device.

18. Dialysis machine according to claim 15, characterized in that the intracellular and extracellular fractions of the fluid are determined.

19. Dialysis machine comprising a dialyzer and at least one device according to claim 9.

20. Device according to claim 9, wherein the at least one coupling coil is an exterior coil and for generating a magnetic field.

21. Device according to claim 9, wherein the inductive coupling-in is supplied via a plurality of coupling coils.

22. Device according to claim 9,
wherein the capacitive measurement forms a high-pass filter,
wherein the electrical measurement value generated in the fluid to be measured by a low-frequency end of the measurement signal is coupled-out inductively by coupling coils, and wherein the electrical measurement value generated in the fluid to be measured by a high-frequency end of the measurement signal is coupled-out capacitively.

23. Device according to claim 9, wherein the coupled-in measurement signal is at least one of an alternating electrical, alternating electromagnetic, or alternating magnetic field frequency-modulated over a frequency of 5 kHz to 1 MHz.

* * * * *